(12) United States Patent
Lazarof

(10) Patent No.: US 11,400,235 B2
(45) Date of Patent: Aug. 2, 2022

(54) ANESTHESIA APPLICATORS/INJECTORS FOR DENTAL AND OTHER APPLICATIONS AND METHODS OF USE

(71) Applicant: Sargon Lazarof, Encino, CA (US)

(72) Inventor: Sargon Lazarof, Encino, CA (US)

(*) Notice: Subject to any disclaimer, the term of this patent is extended or adjusted under 35 U.S.C. 154(b) by 0 days.

(21) Appl. No.: 16/512,102

(22) Filed: Jul. 15, 2019

(65) Prior Publication Data

US 2019/0336704 A1    Nov. 7, 2019

Related U.S. Application Data

(63) Continuation of application No. 15/632,197, filed on Jun. 23, 2017, now Pat. No. 10,391,265, which is a (Continued)

(51) Int. Cl.
*A61M 5/32* (2006.01)
*A61M 5/42* (2006.01)
(Continued)

(52) U.S. Cl.
CPC .............. *A61M 5/3286* (2013.01); *A61C 5/40* (2017.02); *A61M 5/178* (2013.01); (Continued)

(58) Field of Classification Search
CPC ........... A61C 19/08; A61C 19/06; A61C 3/03; A61C 5/062; A61M 2005/3258; (Continued)

(56) References Cited

U.S. PATENT DOCUMENTS 2,904,225 A    9/1959    Earles
3,976,070 A    9/1976    Dumont
(Continued)

FOREIGN PATENT DOCUMENTS

CN    101027096 A    8/2007
DE    202012002829    3/2013
(Continued)

OTHER PUBLICATIONS

Office Action for BR112016000430-2 dated Apr. 22, 2020, 4 pages.
(Continued)

*Primary Examiner* — Jason E Flick
(74) *Attorney, Agent, or Firm* — Kilpatrick Townsend & Stockton LLP

(57) ABSTRACT

Disclosed are applicators and methods injecting of a liquid anesthetic into a dental patient with no or minimal pain. In accordance with one embodiment the applicator is for intraligamentary injection and includes an elongated, thin member having an open distal free formed of a resilient and somewhat conformable material suitable for producing a substantially fluid-tight interface with the anatomic structures at the gingival sulcus to inject the anesthetic therein. In another embodiment the applicator includes a flexible skirt surrounding a sharpened cannula, with the cannula being movable with respect to the skirt. The skirt is arranged to receive the anesthetic to anesthetize the gum, whereupon the cannula can then pierce the gum to inject the anesthetic into the underlying anatomic structure.

7 Claims, 2 Drawing Sheets

Related U.S. Application Data continuation of application No. 14/679,321, filed on Apr. 6, 2015, now Pat. No. 9,687,606, which is a continuation-in-part of application No. 13/938,686, filed on Jul. 10, 2013, now Pat. No. 9,713,680.

(51) Int. Cl.

| | | |
|---|---|---|
| *A61N 1/36* | (2006.01) | |
| *A61N 1/04* | (2006.01) | |
| *A61M 5/178* | (2006.01) | |
| *A61C 5/40* | (2017.01) | |
| *A61M 19/00* | (2006.01) | |
| *A61M 5/31* | (2006.01) | |

(52) U.S. Cl.
CPC .......... *A61M 5/3287* (2013.01); *A61M 5/422* (2013.01); *A61M 19/00* (2013.01); *A61N 1/0456* (2013.01); *A61N 1/36021* (2013.01); *A61M 2005/3107* (2013.01); *A61M 2005/3258* (2013.01); *A61M 2005/3267* (2013.01); *A61M 2202/048* (2013.01); *A61M 2202/30* (2013.01); *A61M 2205/195* (2013.01); *A61M 2210/0631* (2013.01); *A61M 2210/0637* (2013.01)

(58) Field of Classification Search
CPC .... A61M 2005/3267; A61M 2205/195; A61M 5/178; A61M 5/3287; A61M 5/422; A61N 1/0456; A61N 1/36; A61N 1/36021
See application file for complete search history.

(56) References Cited

U.S. PATENT DOCUMENTS

| | | | |
|---|---|---|---|
| 5,178,607 A | 1/1993 | Lynn et al. | |
| 5,749,727 A | 5/1998 | Dao et al. | |
| 5,829,976 A | 11/1998 | Green | |
| 5,885,255 A | 3/1999 | Jaeger et al. | |
| 6,629,958 B1 | 10/2003 | Spinello | |
| 9,687,606 B2 | 6/2017 | Lazarof | |
| 9,713,680 B2 | 7/2017 | Lazarof | |
| 2005/0065473 A1 | 3/2005 | Martn | |
| 2005/0113768 A1 | 5/2005 | Patrickson | |
| 2009/0130628 A1 | 5/2009 | Viscomi | |
| 2009/0216203 A1 | 8/2009 | Ahn | |
| 2012/0045732 A1* | 2/2012 | Chen | A61C 5/62 433/90 |
| 2013/0158560 A1 | 6/2013 | Gleason et al. | |
| 2014/0031747 A1 | 1/2014 | Ardehali | |
| 2015/0018801 A1 | 1/2015 | Lazarof | |
| 2015/0209520 A1 | 7/2015 | Lazarof | |

FOREIGN PATENT DOCUMENTS

| | | |
|---|---|---|
| JP | 08243160 | 9/1996 |
| JP | 2011513036 A | 4/2011 |
| JP | 2012211125 | 11/2012 |
| WO | 9312732 | 7/1993 |
| WO | 9725932 A1 | 7/1997 |
| WO | 2009117464 A1 | 9/2009 |
| WO | 2009146930 A1 | 12/2009 |

OTHER PUBLICATIONS

Office Action for AE23/2016 dated May 30, 2020, 13 pages.
AU2014287554, "First Examination Report", dated Apr. 26, 2018, 6 pages.
AU2019202917, "First Examination Report", dated Feb. 5, 2020, 3 pages.
CN201480042583.2, "Office Action", dated Sep. 29, 2019, 9 pages.
JP2019-000303, "Office Action", dated Feb. 4, 2020, 8 pages.
International Search Report of PCT Application No. PCT/US2014/045523, dated Dec. 16, 2014.
Application No. CA2,917,885, Office Action, dated Feb. 5, 2021, 3 pages.
Application No. JP2019-000303, Office Action, dated Jan. 26, 2021, 7 pages.

* cited by examiner

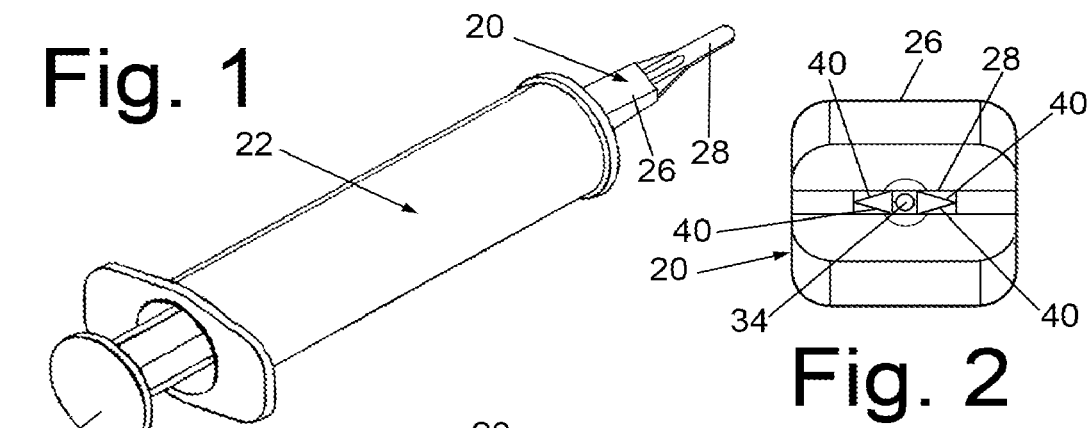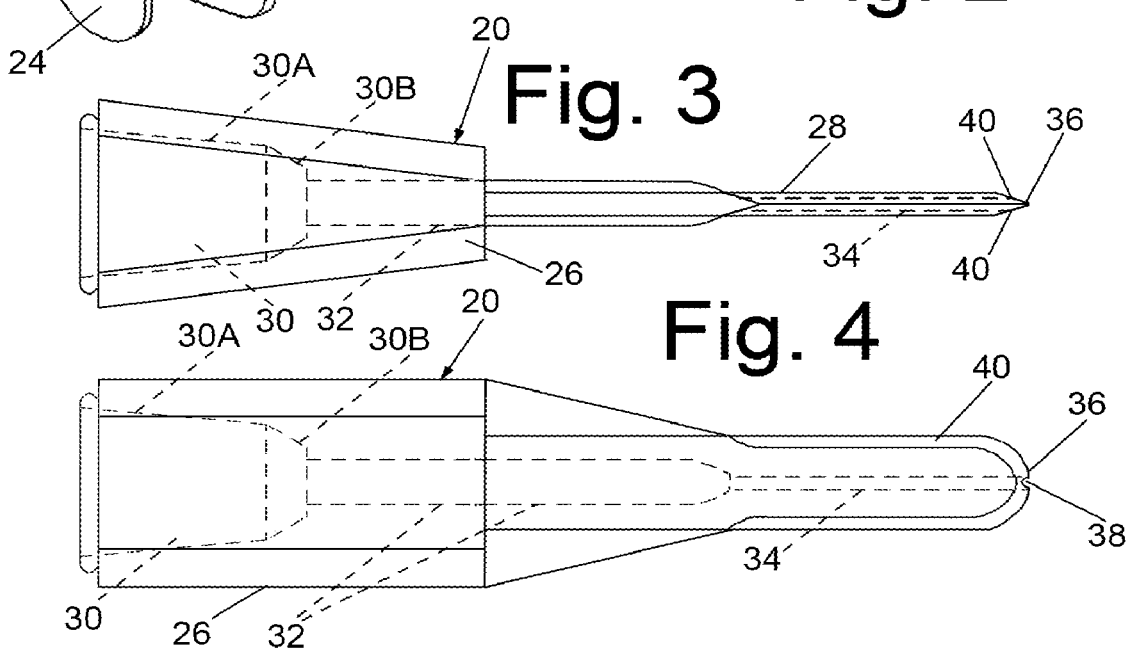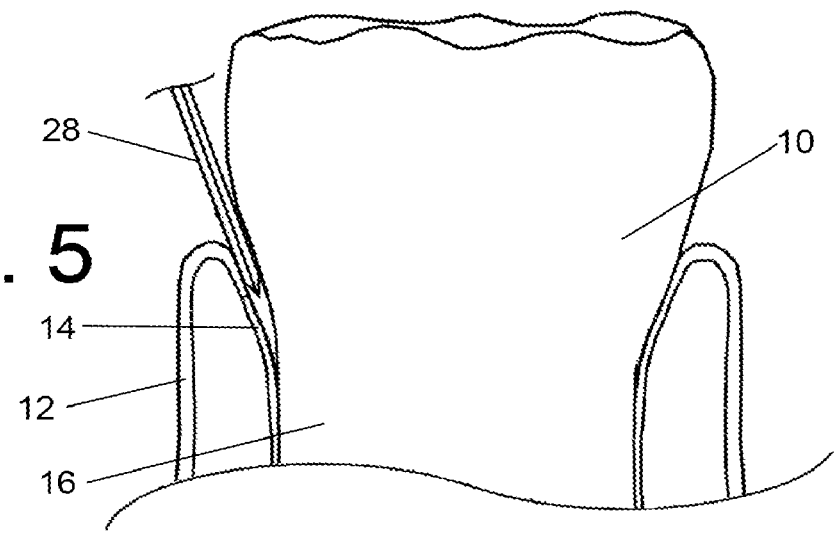

ANESTHESIA APPLICATORS/INJECTORS FOR DENTAL AND OTHER APPLICATIONS AND METHODS OF USE

This application is a continuation application of U.S. patent application Ser. No. 15/632,197 filed Jun. 23, 2017, entitled "ANESTHESIA APPLICATORS/INJECTORS FOR DENTAL AND OTHER APPLICATIONS AND METHODS OF USE," which is a continuation application of U.S. patent application Ser. No. 14/679,321 filed Apr. 6, 2015, now U.S. Pat. No. 9,687,606, entitled "ARTICULATING APPLICATORS/INJECTORS FOR ADMINISTRATION OF LIQUID ANESTHETIC AND OTHER LIQUID," which is a continuation-in-part of application of U.S. patent application Ser. No. 13/938,686 filed Jul. 10, 2013, now U.S. Pat. No. 9,713,680, entitled "ANESTHESIA APPLICATORS/INJECTORS FOR DENTAL AND OTHER APPLICATIONS AND METHODS OF USE," The contents of the aforementioned applications are hereby incorporated by reference in their entirety.

FIELD OF THE INVENTION

This invention relates generally to dental instruments and more particularly to devices and methods of use for injecting a liquid anesthetic during periodontal or other dental procedures, but which can be used for other procedures involving the injection of a liquid into tissue in the body of a living being.

BACKGROUND OF THE INVENTION

As is known, the periodontal ligament injection ("PDL") is an accepted intraligamentary injection modality for primary anesthesia for one or two teeth. It is also used as a supplement to infiltration or block techniques. The PDL technique entails use of a small amount of anesthetic to produce instant anesthesia. In particular, an ultra-short needle is placed in the gingival sulcus on the mesial and distal surfaces and advanced along the root surface until resistance is met. Then the needle is advanced further to make contact and dispense more anesthetic liquid. This allows the numbing of the tooth without the patient feeling the process. The technique's primary advantage is that it provides pulpal anesthesia for 30 to 45 minutes without an extended period of soft tissue anesthesia. Moreover, because only a small amount of liquid anesthetic is injected at the site of the periodontal ligament (which inherently has limited blood circulation) PDL can be used in patients with bleeding disorders.

Various syringes and techniques have been proposed and used in the prior art for effecting PDL and there are even computer controlled anesthetic delivery systems, e.g., "The Wand" offered by Milestone Scientific, of Livingston, N.J. Such prior art syringes, techniques and systems, while suitable for their intended purposes, nevertheless leave something to be desired from one or more of the following standpoints: trauma, patient fear of needles, simplicity, cost, ease of use and effectiveness. Thus, a need exists for a low cost, simple device for readily accomplishing a periodontal ligament injection with minimal, if any patient discomfort. The subject invention addresses that need.

In addition, the subject invention also provides a device and method of use for injecting a liquid anesthetic into the gum and underlying tissue of a patient with less pain than accomplished with conventional needle syringes.

SUMMARY OF THE INVENTION

In accordance with one aspect of the invention there is provided an applicator for effecting an intraligamentary injection of a liquid anesthetic into the gingival sulcus of a patient. The applicator basically comprises a body member having an elongated tip. The tip is a generally planar, thin member having an atraumatic free end and a passageway extending therethrough and terminating at the free end of the tip. The applicator is arranged to be secured to a source of liquid anesthetic, whereupon the liquid anesthetic may be selectively introduced into the applicator. The free end of the elongated tip of the applicator is arranged for producing a substantially fluid-tight interface with the anatomic structures at the gingival sulcus, whereupon the liquid anesthetic may be forced from the applicator through the passageway out of the open free end of the tip to enter into the gingival sulcus so that it is directed downward along the root of the adjacent tooth and is prevented from flowing upward and outward.

In accordance with another aspect of this invention there is provided an applicator for effecting an injection of a liquid anesthetic into the tissue of a person. That applicator basically comprises a coupling, an elongated member having a distal end portion in the form of a hollow skirt having a free edge, and an elongated cannula having an open distal end located within the skirt proximally of the free edge. The open distal end of the cannula is sharp. The coupling is arranged for securing the applicator to a source of liquid anesthetic, whereupon the liquid anesthetic may be selectively introduced within the cannula and from there into the hollow skirt. The hollow skirt is formed of a flexible material suitable for producing a substantially fluid-tight interface with the tissue to locally anesthetize the tissue when the liquid anesthetic is introduced into the hollow skirt. The sharp distal end of the cannula is movable relative to the free edge of the hollow skirt to enable the sharp distal end to penetrate the tissue to inject the liquid anesthetic into the tissue. The applicator may optionally include electrodes forming a portion of a transcutaneous electrical nerve stimulation (TENS) unit.

In accordance with another aspect of this invention there is provided a method for effecting an intraligamentary injection of a liquid anesthetic into the gingival sulcus of a patient. That method basically entails providing an applicator comprising an elongated member having a hollow interior, an open distal free end, and a portion located proximally of the open distal free end in communication with the hollow interior. The open distal free end of the elongated member is formed of a resilient and somewhat conformable material. The open distal free end of the elongated member is introduced into the gingival sulcus to engage the anatomic structures at the gingival sulcus wherein the resilient and conformable material at the open distal free end produces a substantially fluid-tight interface thereat. A liquid anesthetic is provided into the hollow interior of the elongated member and through the open distal free end into the gingival sulcus so that the liquid anesthetic is directed downward along the root of the adjacent tooth and is prevented from flowing upward and outward by the fluid-tight interface.

In accordance with another aspect of this invention there is provided a method for effecting an injection of a liquid anesthetic into the tissue of a person. The method basically entails providing an applicator having a distal end portion in the form of a skirt having hollow interior and a peripheral free edge. The applicator also comprises an elongated cannula having an open distal end located within the skirt proximally of the free edge. The open distal end of the cannula is sharp. The hollow skirt is formed of a flexible material. The free edge of the hollow skirt is placed into engagement with the tissue of the person, whereupon the flexible material at the free end of the skirt produces a substantially fluid-tight interface with the tissue. Liquid anesthetic is provided into the hollow interior of the skirt and into engagement with a portion of the tissue bounded by the peripheral free edge of the skirt to anesthetize the tissue thereat. The sharp distal end of the cannula is moved relative to the free edge of the hollow skirt to cause the sharp distal end to penetrate the portion of the tissue to inject the liquid anesthetic therein. The applicator may optionally include electrodes forming a portion of a transcutaneous electrical nerve stimulation (TENS) unit so that the unit may be operated during the injection procedure. By way of example, but not limitation, instead of providing the liquid anesthetic into the hollow interior of the skirt to anesthesize the tissue thereat, the TENs unit can be operated to anesthetize the tissue, whereupon after the tissue has been anesthesized the cannula may be moved to cause its sharp end to penetrate the tissue. The tissue may comprise the gum and underlying tissue of a dental patient or any other tissue of a person.

BRIEF DESCRIPTION OF THE DRAWINGS

FIG. 1 is an isometric view of one exemplary syringe including an anesthesia applicator or injector constructed in accordance with this invention for periodontal ligament injection (intraligamentary injection);

FIG. 2 is an enlarged end view of the applicator shown in FIG. 1;

FIG. 3 is an enlarged side elevation view of the applicator shown in FIG. 1;

FIG. 4 is an enlarged top plan view of the applicator shown in FIG. 1;

FIG. 5 is a greatly enlarged illustration, partially in section, of the exemplary anesthesia applicator/injector of FIG. 1 shown in the process of performing a periodontal ligament injection;

DETAILED DESCRIPTION OF THE PREFERRED EMBODIMENT

Figure 6:
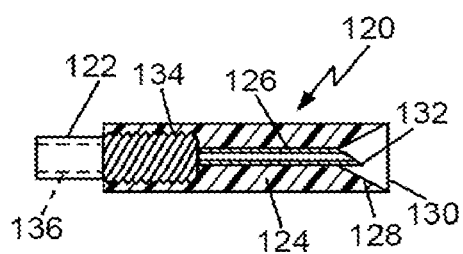
FIG. 6 is a partial sectional view of an alternative anesthesia applicator/injector constructed in accordance with another aspect of this invention, e.g., an injector for penetrating oral tissue.

Referring now to the various figures of the drawings wherein like reference characters refer to like parts, there is shown in FIG. 1 at 20 an applicator or injector mounted constructed in accordance with one exemplary embodiment of this invention shown mounted on a syringe 22 for use in a periodontal procedure. The applicator can be a separate unit or may form an integral part of the syringe. In either case the applicator is connected to the syringe by means of a coupling. In the exemplary embodiment shown in FIGS. 1-4 the applicator is an integral device which is arranged to be mounted on the syringe. The applicator includes a passageway (to be described later) therethrough for enabling the liquid anesthetic to flow therethrough. The syringe 22 can be of any suitable construction so that a liquid anesthetic can be located within a chamber (not shown) in it to be forced from the chamber through into the applicator when desired. To that end the exemplary embodiment of the syringe 22 includes a plunger 24 which when depressed forces the liquid anesthetic out of the syringe's chamber through a coupling (not shown) and into the applicator 20.

It should be pointed out that the applicator 20 may be used with devices, other than a syringe. For example, it can be used with any controlled anesthetic delivery system, like the "The Wand", identified above or with any other equipment, e.g., an electric pump system, arranged to provide a liquid anesthetic under some force.

As best seen in FIGS. 2-4, the applicator 20 basically comprises a hollow proximally located body section 26 from which an elongated tip 28 projects. The tip 28 is a thin, generally planar member which has a generally rectangular profile in cross-section. The body section includes a proximally located chamber 30 (FIGS. 3 and 4) and a distally located chamber 32. The chamber 30 is arranged to receive a bolus of the anesthetic from the syringe when the syringe is actuated. The chamber 30 tapers downward in the distal direction in two sections, 30A and 30B, with the taper in section 30B being more severe than the taper of section 30A. The chamber 32 is in fluid communication with the chamber 30 and is located distally thereof. The chamber 32 serves to produce a jet of the anesthetic liquid from the chamber 30. To that end, the chamber 32 is of a constant diameter, which is less than the diameter of the chamber 30. The chamber 32 extends into the proximal portion of the tip 28.

The tip 28 is preferably formed of a somewhat flexible material, e.g., polypropylene or polycarbonate or any other suitable plastic or other material. A small diameter passageway 34 extends through the tip 28 from its distal end 36 to the distal end of the chamber 32, so that the passageway 34 is in fluid communication with the chamber 32. As best seen in FIG. 4, the distal end 36 of the tip 28 is rounded to be atraumatic and includes a semi-circular shaped cut 38 (FIG. 4) at its distal-most point. The distal end of the passageway 34 terminates at the cut 38 and is in fluid communication therewith.

As mentioned above the tip 28 has a generally flat profile. More precisely, and in accordance with one exemplary preferred embodiment of the invention, the peripheral edge of the distal end portion of the tip is tapered symmetrically at 40. This peripheral taper feature, coupled with the fact that the tip is somewhat flexible facilitates atraumatic entry of the tip into the gingival sulcus.

In one preferred exemplary embodiment of the invention the total length of the applicator 20 is approximately 4 cm (e.g., 2, 3, 4, 5 or 6 cm), with the length of the applicator from its distal end 36 to the proximal end of its chamber 32 being approximately 3 cm (e.g., 1, 2, 3, 4 or 5 cm). The distal portion of the tip 28 is approximately 4 mm (e.g., 2, 3, 4, 5 or 6 mm) wide and 0.5 to 1.0 mm (e.g., 0.5, 0.6, 0.7, 0.8, 0.9 or 1 mm) thick, with the diameter of the passageway 34 being approximately 0.25 mm (e.g., 0.1, 0.2, 0.25, 0.3 or 0.4 mm). The diameter of the chamber 30 at the proximal end of section 30A is approximately 5.4 mm (e.g., 3.0, 4.0, 5.0, 5.4, 6.0 or 7.0 mm), while the internal diameter of the proximal end of the section 30B is approximately 3.5 mm (e.g., 2.0, 3.0, 3.5, 4.0 or 5.0 mm). The diameter of chamber 32 is approximately 2.5 mm (e.g., 1.0, 2.0, 2.5, 3.0 or 4.0 mm), while its length is approximately 1.7 cm (e.g., 0.5, 1.0, 1.7, 2.0, 2.5 or 3.0 cm).

It should be pointed out that the foregoing dimensions are merely exemplary and other shapes and sizes of the applicator 20 are contemplated so long as they enable the distal end of the applicator to be atraumatically introduced into the gingival sulcus along the periodontal ligament to engage the anatomic structures at the gingival sulcus to inject the liquid anesthetic therein.

Operation of the applicator/injection can best be appreciated by reference to FIG. 5. In particular, as shown therein the tip 28 of the applicator 20 is arranged to be atraumatically introduced into the gingival sulcus between the tooth 10 and the gingiva (gum) 12 along the periodontal ligament 14 to engage the anatomic structures thereat. The periphery of the distal portion of the tip being tapered and somewhat flexible forms or produces a fluid tight seal with the immediately adjacent anatomic structures. Thus, when the plunger 24 of the syringe 22 is pressed inward, a jet of the anesthetic liquid produced in the chamber 32 is forced through the communicating passageway 34 out through its open distal end at the cut 38 so that the anesthetic set is directed downward along the root 16 of the adjacent tooth 10 and is prevented from flowing upward and outward by the fluid-tight interfacial seal formed by the free end of the tip.

As should be appreciated by those skilled in the art the use of the thin, flexible tip of the applicator 20 enables one to readily deliver an anesthetic solution through the periodontal membrane, thus doing away with the use of needles. However, it is also within the scope of the invention to place the applicator over a conventional needle and deliver the anesthetic solution through the needle and applicator while preventing the needle from contacting the patient.

Figure 7:
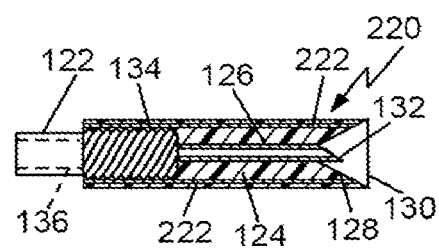
FIG. 7 is a partial sectional view of still another alternative anesthesia applicator/injector constructed in accordance with another aspect of this invention, e.g., a device like that of FIG. 5 but including a electrodes of a transcutaneous electrical nerve stimulation (TENS) unit to facilitate further pain reduction.
Figure 8:
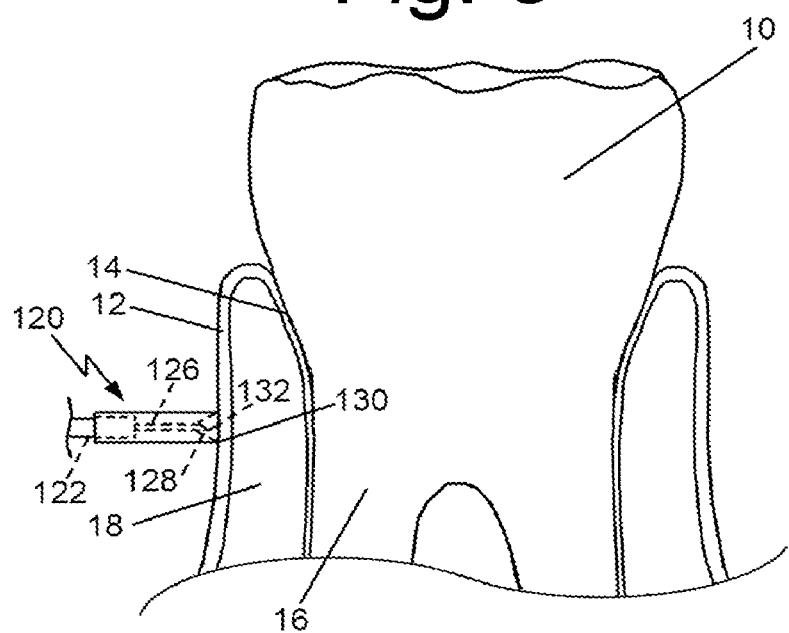
FIG. 8 is an illustration, similar to the illustration of FIG. 4, but showing the applicator/injector of FIG. 5 in the process of performing an injection of through the gingiva.

Turning now to FIGS. 6-8 there is disclosed another exemplary embodiment of an injector 120 constructed in accordance with this invention. This embodiment and variants encompassed by this invention is primarily arranged for infiltration to numb teeth, which heretofore has been accomplished by use of a sharp cannula to pierce the oral tissue adjacent the roots of the teeth to cause the teeth to numb. To that end, the applicator 120, like the applicator 20 is arranged to be used with a syringe (e.g., it may be a separate unit arranged to be mounted on a syringe or may be an integral part of the syringe) or may be used with any controlled anesthetic delivery system, like the "The Wand", identified above or with any other device arranged to provide a liquid anesthetic under some force. Unlike the applicator 20 of FIGS. 1-4, the applicator 120 is arranged to penetrate the gingiva to deliver the liquid anesthetic therethrough. However, like the applicator 20, the applicator injector 120 achieves that end in an atraumatic manner.

As best seen in FIG. 7, the applicator 120 basically comprises a coupling 122, an elongated tubular body 124 and an elongated cannula 126. The elongated tubular body is formed of a somewhat flexible material, e.g., silicone, and has a distal end portion in the form of a hollow skirt 128 having a free edge 130. The cannula 126 is an elongated tubular member formed of any suitable material, e.g., silicone which is more rigid, than the silicone of the body 124. The cannula 126 has a sharpened, open distal free end 132. The cannula 126 extends through the tubular body 124 so that its open free end 132 is in fluid communication with the hollow skirt 128, e.g., the free end 132 may be located within the hollow skirt 128 (show) or may be retracted slightly from it but still in fluid communication with it. The hollow body 124 is mounted on the coupling 122 via a threaded engaging portion 134. The coupling 122 includes a passageway 136 which is in fluid communication with the interior passageway of the cannula and also with the outlet passageway of the chamber in the syringe in which the liquid anesthetic is located.

The periphery of the free edge 130 of the skirt 128 of the applicator/injector 120 is arranged to be brought into engagement with the surface of the gingiva where the injection is to be made, like shown in FIG. 8, whereupon the free edge 130 of the skirt 128 forms a substantially fluid tight seal with the outer surface of gingiva 12 thereat. Accordingly, when the syringe 22 is operated, e.g., its plunger 26 depressed, the liquid anesthetic is forced out of the syringe's chamber through the coupling's passageway 136, into the cannula 126 and out the open end 132 of the cannula, whereupon the anesthetic will be within the skirt and thus in engagement with the portion of the gingiva bounded by the periphery of the free edge of the skirt. This initial dose of the anesthetic serves to locally anesthetize the gingiva, so that once that has occurred the cannula can be used to penetrate the gingiva to a desired depth therebelow to deliver a second dose of the anesthesia, without causing the patient to experience any pain or discomfort. To that end, the cannula 126 is arranged to be moved with respect to the free edge 130 of the skirt 128 so that it can extend distally therebeyond to inject the anesthetic through the gingiva into the underlying structure after the gingiva has been locally anesthetized. For example, the cannula may be threadedly coupled to the body 124 so that its sharp free end can be extended beyond the beyond the free edge 130 of the skirt and into the underlying structure by merely twisting a portion of the applicator 120. Alternatively, the cannula may be coupled to the body so that its sharp free end can be extended beyond the free edge of the skirt by a sliding action, instead of a twisting action. In fact, it is even contemplated that the skirt portion 128 of the body 124 may be constructed so that it is collapsible, bendable or otherwise deformable, so that the sharpened free end of the cannula can be extended therebeyond by pushing on the applicator 120 after the free edge of the skirt has engaged the gingiva and the gingiva has been locally anesthetized to cause the skirt to collapse, bend or otherwise deform.

In any case, the cannula is arranged to move relative to the skirt from a retracted position, like shown in FIGS. 6 and 7, to an extended position (not shown) wherein the sharpened free end of the cannula extends beyond the free edge 130 of the skirt through the gingiva and into the underlying anatomic structure to a desired depth, e.g., into the bone 18, after the gingiva has been locally anesthetized by the anesthetic in the hollow skirt. At that point the plunger of the syringe can be depressed again to inject a dose of the anesthetic into that underlying anatomic structure.

In the interest of making the injection procedure as atraumatic as possible, the distal edge 130, if not the whole body 124 or skirt 128, is formed of a resilient and conformable material. Preferably, the distal free end is also somewhat rounded in shape to form an atraumatic end surface.

In FIG. 7, there is shown an alternative embodiment of an applicator/injector 220, which is constructed similarly to the applicator 120. Thus, in the interest of brevity the structural details of the applicator 220 which are the same as those of the applicator 120 will be given the same reference numbers and the details of their construction and operation will not be reiterated. The applicator 220 includes a pair of electrodes 222 which are located within the tubular body 124 and which are connected to a remote TENS unit (not shown) via a pair of electrical conductors (not shown). Thus the TENS unit can be operated to numb the tissue prior to the cannula's penetration of the tissue, thus further lessening the chance that the patient will experience pain during the injection procedure.

It should be pointed out at this juncture that the embodiments of the applicator/injectors of FIGS. 6 and 7 are not limited to infiltration usage as just described. Hence they can be used for PDL procedures as well. For such usage the applicator has to be appropriately sized and shaped to enter the gingival sulcus. Once the distal end of the applicator/injector 120 or 220 has entered that region the syringe can be operated to inject the liquid anesthetic into the skirt 128, where it will engage and locally anesthetize the adjacent tissue/anatomic structure. Once that small area has been exposed to the anesthetic for a sufficient time to be numbed, the cannula 126 can then be moved relative to the free edge 130 of the skirt to cause it to penetrate the underlying tissue/anatomic structure, whereupon a second dose of the anesthetic may be injected to numb the tooth.

Moreover the applicator 120 is not limited to dental use. Thus, it can be used to inject a liquid anesthetic (or any other liquid substance, for that matter) into any tissue of a patient atraumatically.

It should also be pointed out that the particular materials used to form the applicator/injectors as described above are merely exemplary of various materials which may be used.

Without further elaboration the foregoing will so fully illustrate my invention that others may, by applying current or future knowledge, adopt the same for use under various conditions of service.

I claim:

1. An applicator for effecting an intraligamentary injection of a liquid anesthetic from a compartment of a pump system into a gingival sulcus of a dental patient, the pump system providing a force of the liquid anesthetic from the compartment, the applicator comprising:
   an elongated tip having a proximal end connected with the compartment of the pump system via a chamber, the tip having a distal free end, the distal free end being tapered and planar, and the elongated tip further having a passageway extending from the chamber through the tip and to the distal free end of the tip, the tapered and planar configuration of the distal free end of the tip being sized and configured for atraumatic entry into the gingival sulcus so that the liquid anesthetic flows from the chamber through the passageway to produce a jet of the liquid anesthetic downward along a root of the tooth in the gingival sulcus, and the distal free end of the tip prevents the liquid analgesic from flowing upward and outward from the gingival sulcus of the dental patient.

2. The applicator in accordance with claim 1, wherein the distal free end of the tip is sized and configured for a substantially fluid-tight interface with the gingival sulcus of the dental patient.

3. The applicator in accordance with claim 1, wherein the distal free end of the tip is substantially flat in cross-section.

4. The applicator in accordance with claim 1, wherein a distal end of the tip is flexible.

5. The applicator in accordance with claim 1, wherein a distal end of the tip is formed of plastic.

6. The applicator in accordance with claim 1, wherein a proximal portion of the distal free end of the tip is rounded and wherein a peripheral edge of a distal portion of the tip is tapered.

7. The applicator in accordance with claim 1, wherein tip is 0.5 to 1 mm thick and 2 to 5 mm wide.

* * * * *